United States Patent [19]

Reiter née Esses et al.

[11] Patent Number: 5,064,826
[45] Date of Patent: Nov. 12, 1991

[54] NOVEL TRIAZOLO-PYRIMIDINE DERIVATIVES

[76] Inventors: Klára Reiter née Esses; József Reiter, both of 32/B. Mihályfi E. u., Budapest, Hungary, 1022; Zoltán Budai, 3. Lukács u., Budapest, Hungary; Endre Rivó, 1., Joliot Curie tér, Budapest, Hungary, 1126; Péter Trinka, 59. Karczag u., Budapest, Hungary, 1116; Lujza Petöcz, 2, Rákóczi tér, Budapest, Hungary, 1084; Gábor Gigler, 95. Lenin krt., Budapest, Hungary; István Gyertyán, 9. Összefogás sétány, Budapest, Hungary, 1165; István Gacsályi, 67. Baross u., Budapest, Hungary, 1201

[21] Appl. No.: 487,412

[22] Filed: Mar. 2, 1990

[30] Foreign Application Priority Data

Mar. 3, 1989 [HU] Hungary .............................. 1016/89

[51] Int. Cl.$^5$ .................... A61K 31/38; C07D 495/04; C07D 413/04
[52] U.S. Cl. ................................ 514/233.2; 514/255; 514/267; 544/123; 544/251
[58] Field of Search ................ 544/251, 123; 514/267, 514/258, 255, 233.2

[56] References Cited

U.S. PATENT DOCUMENTS 4,576,943  3/1986  Tomcufcik et al. ................ 514/222
4,831,013  5/1989  Francis ................................ 514/023

OTHER PUBLICATIONS

Chemical Abstracts vol. 110:154252.
Esses Reiter et al., Heterocyclic Chemistry, 1987, 24(6) 1503-1508.

Primary Examiner—Mukund J. Shah
Assistant Examiner—Matthew V. Grumbling
Attorney, Agent, or Firm—Keil & Weinkauf

[57] ABSTRACT

This invention relates to novel triazolopyrimidine derivatives of formulae (Ia) and (Ib),

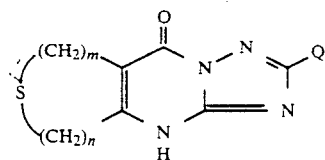

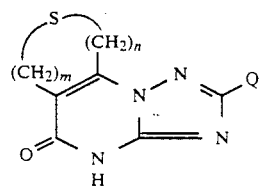

wherein
Q represents hydrogen, a heterocyclic group optionally substituted by a $C_{1-4}$ alkyl group and containing one or more oxygen and/or nitrogen atoms or a group of formula
—SR$^1$ wherein R$^1$ is alkyl or aralkyl, or a group of formula
—NR$^2$R$^3$ wherein R$^2$ and R$^3$ are independently hydrogen, alkyl, alkenyl, cycloalkyl, aralkyl, aryl or a heterocyclic group, m and n are independently 0, 1, 2, 3 or 4, with the provision that if m stands for 0, then n is different from 0, and if both n and m are 1 or m stands for 0 and n is 2, the Q is different from methylthio or morpholino group, their mixtures or pharmaceutically acceptable salts. Furthermore, the invention relates to a process for preparing these compounds.

The compounds of formulae (Ia) and (Ib) are able to inhibit the ptosis caused by tetrabenazine and they have analgetic activity.

7 Claims, No Drawings

NOVEL TRIAZOLO-PYRIMIDINE DERIVATIVES

The present invention relates to novel, pharmaceutically active triazolo-pyrimidine derivatives of formulae Ia and Ib,

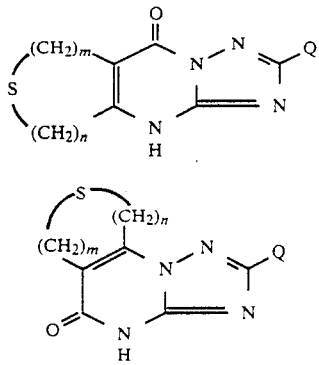

their mixtures and pharmaceutically acceptable salts, pharmaceutical compositions comprising the same as active ingredient, and a process for the preparation of the active ingredients.

In the compounds of formulae Ia and Ib
Q represents hydrogen, a heterocyclic group optionally substituted by a $C_{1-4}$ alkyl group and containing one or more oxygen and/or nitrogen atoms or a group of formula
—$SR^1$ wherein $R^1$ is alkyl or aralkyl, or a group of formula
—$NR^2R^3$ wherein $R^2$ and $R^3$ are independently hydrogen, alkyl, alkenyl, cycloalkyl, aralkyl, aryl or a heterocyclic group,
m and n are independently 0, 1, 2, 3 or 4,
with the proviso that if m stands for 0, then n is different from 0, and if both n and m are 1 or m stands for 0 and n is 2, then Q is different from methylthio or morpholino group.

The present invention covers all the isomers or tautomeric forms of compounds of formula Ia or Ib.

Compounds of formula Ia and Ib exhibit excellent biological activity and low toxicity, e.g. they are able to inhibit the ptosis caused by tetrabenazine, they have analgesic activity and they can be used as starting materials of other pharmaceutically active derivatives as well.

In the specification the terms are defined as follows:
"Heterocyclic group" means a 4 to 8 membered group which can be formed from compounds comprising independently one or more nitrogen and/or oxygen atoms or a group which can be obtained by condensing the same compounds with each other or with benzene. Such groups may be aromatic or partially or completely saturated and may be substituted by one or more substituents.

As examples for such groups e.g. piperidinyl, morpholinyl, piperazinyl, furyl, imidazolyl, pyridinyl, pyrimidinyl, benzofuranyl, indolyl, isoquinolyl, naphthyridinyl, isoxazolyl, isoindolyl or their partially or completely saturated derivatives may be mentioned.

The substituents of the heterocyclic group may preferably be e.g. one or more halogens, alkyl optionally substituted by hydroxy group or alkoxy, amino, nitro, hydroxyl group, etc.

"Alkyl group" means a straight or branched alkyl group having 1 to 12 carbon atoms, e.g. methyl, ethyl, octyl, i-butyl, t-butyl, dodecyl group.

"Alkoxy group" means a straight or branched alkoxy group having 1 to 12 carbon atoms, e.g. methoxy, i-butoxy, t-butoxy, dodecyloxy group.

"Cycloalkyl group" means a cyclic alkyl group having 3 to 8 carbon atoms, e.g. cyclopropyl, cyclohexyl, cyclooctyl group.

"Aralkyl group" means phenylalkyl or naphthylalkyl having 1 to 4 carbon atoms in the alkyl moiety, both being optionally substituted by one or more substituents. The preferred substituents are the same as listed for the "heterocyclic group".

"Aryl group" means phenyl or naphthyl group, both being optionally substituted by one or more substituents. The preferred substituents are the same as listed for the "heterocyclic group".

The preferred compounds of formulae Ia and Ib are those wherein Q represents a group of formula —$NR^2R^3$, wherein $R^2$ and $R^3$ independently stand for alkyl having 1 to 6 carbon atoms optionally substituted by phenyl, alkenyl having 2 to 4 carbon atoms or cycloalkyl having 3 to 6 carbon atoms, phenylalkyl having 1 to 4 carbon atoms in the alkyl moiety.

In an other preferred group of compounds of formulae Ia and Ib Q represents piperidino, morpholino or piperazino optionally substituted by alkyl having 1 to 4 carbon atoms.

In a further preferred group of compounds of formulae Ia and Ib Q represents —$SR^1$, wherein $R^1$ stands for alkyl having 1 to 4 carbon atoms.

The pharmaceutically acceptable salts of compounds of formulae Ia and Ib are the salts formed with alkali metal ions, preferably the potassium or sodium salt, or the acid addition salts of compounds of formulae Ia and Ib formed with pharmaceutically acceptable strong inorganic or organic acids. As examples for the acid-addition salts the hydrochloride, hydrobromide, hydroiodide, sulfate, nitrate, methanesulfonate salts can be mentioned.

According to the invention the compounds of formulae Ia and Ib, the mixture or the pharmaceutically acceptable salts thereof are prepared by reacting a triazole derivative of formula II

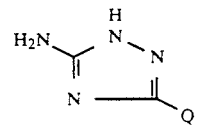

wherein Q is the same as defined hereinabove—with a cyclic beta-keto-ester of formula III

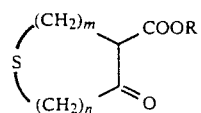

wherein m and n are the same as defined hereinabove, then, if desired, separating the isomers of formulae Ia and Ib from each other.

The starting materials can be reacted in a solvent. The solvent may be an aprotic, protic, polar or dipolar-aprotic, etc. solvent. As examples for such solvents dimethyl formamide, acetic acid, chlorobenzene, and butanol can be mentioned. A solvent mixture can also be used. The reactants can be reacted with each-other without using a solvent, in the form of a melt. The reaction can be carried out at a temperature of 80° to 250° C., preferably at a temperature of 100° to 150° C. The reaction can very preferably be carried out at the boiling point of the solvent used.

The compounds of formulae Ia and Ib can be recovered from the reaction mixture very easily by simple filtration as they usually crystallize out from the reaction mixture. If the products do not crystallize out from the reaction mixture, they can be precipitated by using a solvent which does not dissolve or poorly dissolves the compounds of formulae Ia and Ib, e.g. water, i-propanol or ethyl acetate, then the product can be recovered by filtration.

The separation of the isomers of compounds of formulae Ia and Ib can be carried out after a simple recrystallization from a suitable solvent. Such kind of separation is especially preferred when sodium salt is formed from the isomeric mixture of compounds of formulae Ia and Ib in warm water, methanol or dimethylformamide with the aid of sodium hydroxide, and after cooling down the reaction mixture the sodium salt of the isomer Ia precipitates from the mixture practically in quantitative yield, while the sodium salt of isomer Ib remains in the solution. The sodium salts thus obtained can separately be acidified with glacial acetic acid in aqueous solution and thus the pure isomers of compounds of formulae Ia and Ib can be obtained.

The compounds of formula II used as starting materials are known or can be prepared in a manner analogously with the known compounds. (J. Heterocyclic Chem. 19, 1157/1983/, J. Heterocyclic Chem. 23, 401/1986/).

The cyclic beta-keto-esters of formula III are also known compounds or can be prepared in a manner analogously with the known compounds. (J. Am. Chem. Soc. 74, 1569/1952/; Mh. Chem. 104, 1520/1973/, J. Am. Chem. Soc. 70, 1813/1948/; J. Am. Chem. Soc. 74, 917/1952/).

If desired, the compounds of formulae Ia and Ib can be transformed into their pharmaceutically acceptable acid-addition salts. The salt formation can be carried out in a manner known per se, by reacting a base of formula Ia and/or Ib and a suitable acid of molar equivalent amount in an inert organic solvent.

The alkaline metal salts of compounds of formulae Ia and Ib can be prepared e.g. with the aid of potassium or sodium hydroxide in aqueous or dimethyl formamide solution.

The pharmacological activity of compounds of formulae Ia and Ib is verified as follows.

TABLE I

Antidepressant activity of some of compounds of formulae Ia and Ib shown against tetrabenazine ptosis (T.P.) and analgesic activity in Writhing test (W.t.) after p.o. administration

| No. of Example | T.P. ED$_{50}$ (mg/kg) | TI | W.t. ED$_{50}$ (mg/kg) | TI |
|---|---|---|---|---|
| 18 | | | 375 | 5.3 |
| 19 | 2.7 | 748 | | |
| 21 | 5.2 | 385 | | |
| 25 | 22.5 | 87 | | |
| 26 | | | 355 | 5.6 |
| paracetamol | | | 421 | 2.8 |

TABLE I-continued

Antidepressant activity of some of compounds of formulae Ia and Ib shown against tetrabenazine ptosis (T.P.) and analgesic activity in Writhing test (W.t.) after p.o. administration

| No. of Example | T.P. ED$_{50}$ (mg/kg) | TI | W.t. ED$_{50}$ (mg/kg) | TI |
|---|---|---|---|---|
| amitriptyline | 12.0 | 19 | | |

TI = therapeutical index = LD$_{50}$/ED$_{50}$
paracetamol = p-(acetylamino)-phenol
amitriptyline = 5-(3-dimethylaminopropylidene)dibenz/a,d/1,4-cycloheptadiene The compounds of formulae Ia and Ib and pharmaceutically acceptable acid addition salts thereof can be used in therapeutical practice in the form of pharmaceutical formulations comprising the active ingredient together with one or more inert, non-toxic solid or liquid carriers. The pharmaceutical formulations may be suitable for oral administration (e.g. tablet, coated tablet, dragee, solid or soft gelatin capsule, solution, emulsion or suspension) or parenteral administration (e.g. injection solution) or rectal administration (e.g. suppository).

The pharmaceutical formulations can be prepared according to commonly known methods, i.e. by mixing the active ingredient and the inert inorganic or organic, solid or liquid carriers and forming a pharmaceutical formulation.

As carrier for the preparation of tablets, coated tablets, dragees and solid gelatine capsules e.g. lactose, corn starch, potatoe starch, talc, magnesium carbonate, magnesium stearate, calcium carbonate, stearic acid or the salts thereof, etc. can be used. As carrier for the soft gelatin capsules e.g. vegetable oils, fats, waxes or polyols of suitable consistency can be used. As carriers for the solutions and syrups e.g. water, polyols, polyethylene glycol, sacharose or glucose can be used. The injection solutions can comprise e.g. water, alcohols, polyols, glycerol or vegetable oils as carrier. The suppositories can be prepared with the aid of e.g. oils, waxes, fats or polyols of suitable consistency.

In addition, the pharmaceutical formulations may comprise excipients usually applied in pharmaceutical industry, e.g. wetting, sweetening agents, aroma substances, salts causing the change of osmotic pressure, buffers, etc. The pharmaceutical formulations may further comprise other active ingredients which do not exhibit synergistic effect together with compounds of formulae Ia and/or Ib.

The compounds of formulae Ia and/or Ib can preferably be used in therapy orally in the form of tablets or capsules. Especially preferred are the capsules or tablets comprising 2.5 to 50 mg of active ingredient.

The daily dose of compounds of formulae Ia and/or Ib can vary within wide ranges depending on several factors, e.g. on the activity of the active ingredient, the patient's condition and age, the severity of the disease, etc. The preferred oral dose is generally 1 to 10.000 mg/day, more preferably 150 to 200 mg/day. It has to be stressed that the above doses are only of informative character and the administered dose must always be determined by the physician therapeutist.

The invention is further illustrated by the following, non-limiting examples.

The percent values of sodium hydroxide solutions mean "g/100 ml solution".

EXAMPLE 1

2-Dimethylamino-6,8-dihydrothieno[3,4-d]-1,2,4-triazolo-[1,5-a]pyrimidine-5(9H)-one To 19.1 g (0.15 mole) of 5-amino-3-dimethylamino-1H-1,2,4-triazole dissolved in 15 ml of acetic acid 24.3 g (0.15 moles) of methyl 4-oxo-tetrahydrothiophene-3-carboxylate are added and the reaction mixture is boiled for 15 minutes. The product precipitated from the reaction mixture is filtered off from the hot solution, then washed with i-propanol and recrystallized from dimethylformamide. Thus 26.1 g (73.3%) of 2-dimethylamino-6,8-dihydrothieno[3,4-d]-1,2,4-triazolo-[1,5-a]pyrimidine-5(9H)-one are obtained. Melting point: 355°–360° C.

Proceeding according to Example 1, using the appropriate 5-amino-1,2,4-triazoles of formula II the following further compounds are prepared:

EXAMPLE 2

2-Diallylamino-6,8-dihydrothieno[3,4-d]-1,2,4-triazolo-[1,5-a]pyrimidine-5(9H)-one Yield: 51.2%. M.p.: 260°–265° C. (after recrystallization from dimethylformamide).

EXAMPLE 3

2-(2-Phenyl-ethylamino)-6,8-dihydrothieno[3,4-d]-1,2,4-triazolo-[1,5-a]pyrimidine-5(9H)-one Yield: 63.2%. M.p.: 295°–297° C. (after recrystallization from dimethylformamide).

EXAMPLE 4

2-Cyclohexylamino-6,8-dihydrothieno[3,4-d]-1,2,4-triazolo-[1,5-a]pyrimidine-5(9H)-one Yield: 51.0%. M.p.: higher than 350° C. (after recrystallization from dimethylformamide).

EXAMPLE 5

2-(t-Butylamino)-6,8-dihydrothieno[3,4-d]-1,2,4-triazolo-[1,5-a]pyrimidine-5(9H)-one Yield: 62.8%. M.p.: higher than 260° C. (after recrystallization from dimethylformamide).

EXAMPLE 6

2-Piperidino-6,8-dihydrothieno[3,4-d]-1,2,4-triazolo-[1,5-a]pyrimidine-5(9H)-one Yield: 73.6%. M.p.: higher than 350° C. (after recrystallization from dimethylformamide).

EXAMPLE 7

2-(4-Methyl-piperazino)-6,8-dihydrothieno[3,4-d]-1,2,4-triazolo-[1,5-a]pyrimidine-5(9H)-one Yield: 83.8%. M.p.: 306°–310° C. (after recrystallization from 80% aqueous ethanol).

EXAMPLE 8

2-Dimethylamino-6,8-dihydrothieno[3,4-d]-1,2,4-triazolo-[1,5-a]pyrimidine-5(9H)-one and 2-dimethylamino-5,7-dihydrothieno[3,4-e]-1,2,4-triazolo-[1,5-a]pyrimidine-8(9H)-one To 19.1 g (0.15 mole) of 5-amino-3-dimethylamino-1H-1,2,4-triazole dissolved in a mixture of 40 ml of dimethylformamide and 10 ml of acetic acid 24.3 g (0.15 mole) of methyl 4-oxo-tetrahydrothiophene-3-carboxylate are added and the reaction mixture is boiled for 10 minutes. The product precipitates from the warm reaction mixture. After cooling the reaction mixture is diluted with 80 ml of i-propanol and the precipitated crystals are filtered off.

Thus 31 g (82.2%) of crude product are obtained which is the mixture of 2-dimethylamino-6,8-dihydrothieno-[3,4-d]-1,2,4-triazolo-[1,5-a]pyrimidine-5(9H)-one and 2-dimethylamino-5,7-dihydrothieno[3,4-e]-1,2,4-triazolo-[1,5-a]pyrimidine-8(9H)-one. The mixture is recrystallized from 600 ml of hot dimethylformamide.

Thus 27.0 g (75.8%) of 2-dimethylamino-6,8-dihydrothieno[3,4-d]-1,2,4-triazolo-[1,5-a]pirimidine-5(9H)-one are obtained. Melting point: 355°–360° C. Having left the mother liquor to stand for a long time, 1.6 g (4.5%) of 2-dimethylamino-5,7-dihydrothieno[3,4-e]-1,2,4-triazolo[1,5-a]pyrimidine-8(9H)-one precipitate. Melting point: 296°–298° C.

Proceeding according to Example 8 the following compounds are prepared by using the appropriate 5-amino-1,2,4-triazole of formula II:

EXAMPLE 9

2-Diallylamino-6,8-dihydrothieno[3,4-d]-1,2,4-triazolo-[1,5-a]pyrimidine-5(9H)-one Yield: 59.3%. M.p.: 262°–265° C. (after recrystallization from dimethylformamide).

EXAMPLE 10

2-Benzylamino-6,8-dihydrothieno[3,4-d]-1,2,4-triazolo-[1,5-a]pyrimidine-5(9H)-one Yield: 65.1%. M.p.: 328°–331° C. (after recrystallization from dimethylformamide).

EXAMPLE 11

2-(2-Phenyl-ethylamino)-6,8-dihydrothieno[3,4-d]-1,2,4-triazolo-[1,5-a]pyrimidine-5(9H)-one Yield: 60.1%. M.p.: 295°–298° C. (after recrystallization from dimethylformamide).

EXAMPLE 12

2-Cyclohexylamino-6,8-dihydrothieno[3,4-d]-1,2,4-triazolo-[1,5-a]pyrimidine-5(9H)-one Yield: 62.9%. M.p.: higher than 350° C. (after recrystallization from dimethylformamide).

EXAMPLE 13

2-Dimethylamino-6,8-dihydrothieno[3,4-d]-1,2,4-triazolo-[1,5-a]pyrimidine-5(9H)-one and 2-dimethylamino-5,7-dihydrothieno[3,4-e]-1,2,4-triazolo-[1,5-a]pyrimidine-8(9H)-one The process according to Example 8 is followed except that the crude mixture (31 g) of 2-dimethylamino-6,8-dihydrothieno[3,4-d]-1,2,4-triazolo-[1,5-a]pyrimidine-5(9H)-one and 2-dimethylamino-5,7-dihydrothieno[3,4-e]-1,2,4-triazolo[1,5-a]pyrimidine-8(9H)-one thus obtained is dissolved in 80 ml of 10% hot sodium hydroxide solution. The 2-dimethylamino-6,8-dihydrothieno[3,4-d]-1,2,4-triazolo-[1,5-a]pyrimidine-5(9H)-one sodium salt (31.7 g, 77%) precipitating upon cooling (melting point: higher than 350° C.) is dissolved in 300 ml of warm distilled water, then the solution is acidified with an excess of acetic acid. Thus 27.2 g (76.4%) of pure 2-dimethylamino-6,8-dihydrothieno[3,4-d]-1,2,4-triazolo-[1,5-a]pyrimidine-5(9H)-one are obtained. (Melting point: higher than 360° C.)

Upon acidifying the mother liquor of the sodium salt 2.1 g (5.9%) of 2-dimethylamino-5,7-dihydrothieno-[3,4-e]-1,2,4-triazolo[1,5-a]pyrimidine-8(9H)-one are obtained with a melting point of 295°–298° C. after recrystallization from dimethylformamide.

EXAMPLE 14

2-Dimethylamino-6,8-dihydrothieno[3,4-d]-1,2,4-triazolo-[1,5-a]pyrimidine-5(9H)-one The process of Example 8 is followed except that the reaction is carried out in 60 ml of dimethylformamide instead of a mixture of acetic acid and dimethylformamide. Yield: 23.7 g (66.5%) of 2-dimethylamino-6,8-dihydrothieno[3,4-d]-1,2,4-triazolo-[1,5-a]pyrimidine-5(9H)-one (melting point: higher than 360° C.) and 2.4 g (6.7%) of 2-dimethylamino-5,7-dihydrothieno[3,4-e]-1,2,4-triazolo-[1,5-a]pyrimidine-8(9H)-one (melting point: 295°–298° C.).

EXAMPLE 15

2-Piperidino-5,7,8,9-tetrahydrothiopyrano[3,2-d]-1,2,4-triazolo[1,5-a]pyrimidine-5(10H)-one 16.7 g (0.1 mole) of 5-amino-3-piperidino-1H-1,2,4-triazole are dissolved in 10 ml of acetic acid and 18.8 g (0.1 mole) of ethyl 3-oxo-3,4,5,6-tetrahydro-2H-thiopyrane-2-carboxylate are added, then the reaction mixture is boiled for 10 minutes. The thick crystal mass thus obtained is diluted with 100 ml of water, the precipitated product is filtered off, washed with i-propanol and recrystallized from dimethylformamide. Thus 23.3 g (82.2%) of 2-piperidino-5,7,8,9-tetrahydrothiopyrano[3,2-d]-1,2,4-triazolo[1,5-a]pyrimidine-5(10H)-one are obtained with a melting point above 350° C.

EXAMPLE 16

2-(4-Methylpiperazino)-5,7,8,9-tetrahydrothiopyrano[3,2-d]-1,2,4-triazolo[1,5-a]pyrimidine-5(10H)-one 16.7 g (0.1 mole) of 5-amino-3-(4-methylpiperazino)-1H-1,2,4-triazole are dissolved in 15 ml of acetic acid, then 18.8 g (0.1 mole) of ethyl 3-oxo-3,4,5,6-tetrahydro-2H-thiopyrane-2-carboxylate are added. The reaction mixture is boiled for 90 minutes. After cooling it is diluted with 200 ml of ethyl acetate. The precipitated product is filtered off and washed with ethyl acetate.

Thus 30.0 g (97.9%) of 2-(4-methylpiperazino-5,7,8,9-tetrahydrothiopyrano[3,2-d]-1,2,4-triazolo-[1,5-a]pyrimidine-5(10H)-one are obtained which melt at 298°–301° C. after recrystalization from 80% aqueous methanol.

EXAMPLE 17

2-(4-Methylpiperazino)-5,7,8,9-tetrahydrothiopyrano-[3,2-d]-1,2,4-triazolo[1,5-a]pyrimidine-5(10H)-one The process of Example 16 is followed except that the 30 g of crude 2-(4-methylpiperazino-5,7,8,9-tetrahydrothiopyrano[3,2-d]-1,2,4-triazolo[1,5-a]pyrimidine-5(10H)-one are dissolved in the solution of 9 g of sodium hydroxide and 90 ml of methanol. The solution is clarified by adding charcoal then evaporated to dryness in vacuo. The residue is boiled with 50 ml of i-propanol, thus the product recrystallizes. The precipitated crystals are filtered off and washed with i-propanol. Thus 28.0 g (85%) of 2-(4-methylpiperazino)-5,7,8,9-tetrahydrothiopyrano-[3,2-d]-1,2,4-triazolo[1,5-a]pyrimidine-5(10H)-one sodium salt are obtained (melting point: above 350° Celsius) which is dissolved in 60 ml of distilled water and the solution is acidified to pH=4 with acetic acid. The precipitated product is filtered off and washed with some methanol. Thus 25.1 g (81.9%) of pure 2-(4-methylpiperazino)-5,7,8,9-tetrahydrothiopyrano-[3,2-d]-1,2,4-triazolo[1,5-a]pyrimidine-5(10H)-one are obtained which melt at 299°–301° C.

EXAMPLE 18

2-Methylthio-5,7,8,9-tetrahydrothiopyrano[3,2-d]-1,2,4-triazolo[1,5-a]pyrimidine-5(10H)-one and 2-methylthio-5,6,7,9-tetrahydrothiopyrano[2,3-e]-1,2,4-triazolo-[1,5-a]pyrimidine-9(10H)-one To the solution of 6.5 g (0.05 mole) of 5-amino-3-methylthio-1H-1,2,4-triazole, 2.5 ml of acetic acid and 12.5 ml of dimethylformamide 9.4 g (0.05 mole) of ethyl 3-oxo-3,4,5,6-tetrahydro-2H-thiopyrane-2-carboxylate are added and the reaction mixture is boiled for 60 minutes. The precipitated product is filtered off from the hot solution, then washed with acetic acid and i-propanol and recrystallized from dimethylformamide. Thus 6.5 g (51.1%) of 2-methylthio-5,7,8,9-tetrahydrothiopyrano[3,2-d]-1,2,4-triazolo[1,5-a]pyrimidine-5(10H)-one are obtained. M.p.: higher than 350° C.

From the ethyl acetate/dimethylformamide reaction mixture 1.8 g (14%) of 2-methylthio-5,6,7,9-tetrahydrothiopyrano[2,3-e]-1,2,4-triazolo-[1,5-a]pyrimidine-9(10H)-one precipitate after cooling which melts at 314°–318° C. after recrystallization from dimethylformamide.

EXAMPLE 19

2-Dimethylamino-5,7,8,9-tetrahydrothiopyrano[3,2-d]-1,2,4-triazolo[1,5-a]pyrimidine-5(10H)-one To the solution of 6.35 g (0.05 mole) of 5-amino-3-dimethylamino-1H-1,2,4-triazole, 2.5 ml of acetic acid and 12.5 ml of dimethylformamide, 9.4 g (0.05 mole) of ethyl 3-oxo-3,4,5,6-tetrahydro-2H-thiopyrane-2-carboxylate are added and the reaction mixture is boiled for 40 minutes. The precipitated product is filtered off from the hot solution, then washed with acetic acid and i-propanol and recrystallized from dimethylformamide. Thus 8.2 g (65.2%) of 2-dimethylamino-5,7,8,9-tetrahydrothiopyrano[3,2-d]-1,2,4-triazolo[1,5-a]pyrimidine-5(10H)-one are obtained. M.p.: higher than 350° C.

Following the procedure according to Example 19, the following compounds are prepared by using the appropriate 5-amino-1,2,4-triazole derivatives of formula II:

EXAMPLE 20

2-Diethylamino-5,7,8,9-tetrahydrothiopyrano[3,2-d]-1,2,4-triazolo[1,5-a]pyrimidine-5(10H)-one Yield of the crude product: 85.3 g (61.1%).

Melting point: 305°–315° C.

The crude product is dissolved in 200 ml of hot 5% sodium hydroxide solution, filtered off and left to crystallize. The precipitated product is filtered off (melting point: 320°–325° C.), dissolved again in 1100 ml of warm water then the solution is acidified with acetic acid. A thick precipitate precipitates at once which is filtered off, washed thoroughly with water and left to dry. Thus 78.5 g (56.2%) of pure 2-diethylamino-5,7,8,9-tetrahydrothiopyrano[3,2-d]-1,2,4-triazolo[1,5-a]pyrimidine-5(10H)-one are obtained with a melting point of 308°–310° C.

EXAMPLE 21

2-Morpholino-5,7,8,9-tetrahydrothiopyrano[3,2-d]-1,2,4-triazolo[1,5-a]pyrimidine-5(10H)-one Yield: 64.8%. M.p.: higher than 350° C. (after recrystallization from dimethylformamide).

EXAMPLE 22

2-Diallylamino-5,7,8,9-tetrahydrothiopyrano[3,2-d]-1,2,4-triazolo[1,5-a]pyrimidine-5(10H)-one Yield: 77.1%. M.p.: 270°–273° C. (after recrystallization from a 2:1 mixture of dimethylformamide and i-propanol).

EXAMPLE 23

2-Benzylamino-5,7,8,9-tetrahydrothiopyrano[3,2-d]-1,2,4-triazolo[1,5-a]pyrimidine-5(10H)-one Yield: 78.2%. M.p.: 330°–335° C. (after recrystallization from dimethylformamide).

EXAMPLE 24

2-(2-Phenylethylamino)-5,7,8,9-tetrahydrothiopyrano[3,2-d]-1,2,4-triazolo[1,5-a]pyrimidine-5(10H)-one Yield: 75.1%. M.p.: 322°–325° C. (after recrystallization from dimethylformamide).

EXAMPLE 25

2-Cyclohexylamino-5,7,8,9-tetrahydrothiopyrano[3,2-d]-1,2,4-triazolo[1,5-a]pyrimidine-5(10H)-one Yield: 72.0%. M.p.: 298°–302° C. (after recrystallization from dimethylformamide).

EXAMPLE 26

2-t-Butylamino-5,7,8,9-tetrahydrothiopyrano[3,2-d]-1,2,4-triazolo[1,5-a]pyrimidine-5(10H)-one Yield: 62.4%. M.p.: 320° C. (after recrystallization from a 2:1 mixture of dimethylformamide and i-propanol).

EXAMPLE 27

2-Benzylamino-5,7,8,9-tetrahydrothiopyrano[3,2-d]-1,2,4-triazolo[1,5-a]pyrimidine-5(10H)-one The process of Example 22 is followed except that the crude 2-benzylamino-5,7,8,9-tetrahydrothiopyrano[3,2-d]-1,2,4-triazolo[1,5-a]pyrimidine-5(10H)-one (13.3 g, 84.9%) is dissolved in 75 ml of hot dimethylformamide, then 20 ml of 10% sodium hydroxide solution are added to the hot solution and after cooling the precipitated 2-benzylamino-5,7,8,9-tetrahydrothiopyrano[3,2-d]-1,2,4-triazolo[1,5-a]pyrimidine-5(10H)-one sodium salt (with 1.5 moles of crystalline water) is filtered off (14.9 g, 82.2%, melting point: higher than 350° C.), dissolved in 200 ml of hot distilled water and acidified with an excess of acetic acid. After filtering the precipitated product 12.4 g (79.1%) of pure 2-benzylamino-5,7,8,9-tetrahydrothiopyrano[3,2-d]-1,2,4-triazolo[1,5-a]pyrimidine-5(10H)-one are obtained. M.p.: 332°–335° C.

EXAMPLE 28

2-Dimethylamino-5,7,8,9-tetrahydrothiopyrano[3,2-d]-1,2,4-triazolo[1,5-a]pyrimidine-5(10H)-one The process of Example 19 is followed except that the crude 10.1 g (80.4%) of 2-dimethylamino-5,7,8,9-tetrahydrothiopyrano[3,2-d]-1,2,4-triazolo[1,5-a]pyrimidine-5(10H)-one are dissolved in 25 ml of hot 10% sodium hydroxide solution and left to crystallize. After cooling the precipitated crystalline sodium salt (10.5 g, 76.8%) (melting point: higher than 350° C.) is filtered off and dissolved in 120 ml of distilled water again, and the solution is acidified with acetic acid. The precipitated crystals are filtered off, thoroughly rinsed with water and dried.

Thus 8.85 g (70.4%) of pure 2-dimethylamino-5,7,8,9-tetrahydrothiopyrano[3,2-d]-1,2,4-triazolo-[1,5-a]pyrimidine-5(10H)-one are obtained. (M.p.: higher than 350° C.)

EXAMPLE 29

2-Methylthio-5,6,7,9-tetrahydrothiopyrano[3,4-d]-1,2,4-triazolo[1,5-a]pyrimidine-5(10H)-one 0.976 g (0.0075 mole) of 5-amino-3-methylthio-1H-1,2,4-triazole are dissolved in 6 ml of acetic acid, then 1.368 g (0.075 mole) of ethyl 3-oxo-3,4,5,6-tetrahydro-2H-thiopyrane-4-carboxylate are added and the reaction mixture is boiled for 30 minutes. The precipitated product is filtered off from the hot solution, washed with water and recrystallized from dimethylformamide. Thus 1.2 g (62.9%) of 2-methylthio-5,6,7,9-tetrahydrothiopyrano[3,4-d]-1,2,4-triazolo[1,5-a]pyrimidine-5(10H)-one are obtained which melt at 294°–297° C.

EXAMPLE 30

2-Methylthio-5,6,8,9-tetrahydrothiopyrano[4,3-d]-1,2,4-triazolo-[1,5-a]pyrimidine-5(10H)-one 1.30 g (0.01 mole) of 5-amino-3-methylthio-1H-1,2,4-triazole are dissolved in 6 ml of acetic acid, then 1.88 g (0.01 mole) of ethyl 4-oxo-3,4,5,6-tetrahydro-2H-thiopyrane-3-carboxylate are added and the reaction mixture is boiled for 60 minutes. The precipitated product is filtered off from the hot solution and washed with i-propanol. The 1.6 g (63%) of 2-methylthio-5,6,8,9-tetrahydrothiopyrano[4,3-d]-1,2,4-triazolo[1,5-a]pyrimidine-5(10H)-one thus obtained are dissolved in 12 ml of hot 10% sodium hydroxide solution and after cooling down the precipitated 2-methylthio-5,6,8,9-tetrahydrothiopyrano[4,3-d]-1,2,4-triazolo[1,5-a]pyrimidine-5(10H)-one sodium salt is filtered off (melting point: higher than 350° C.), then dissolved in 30 ml of distilled water. Thereafter the solution is made highly acidic with the aid of acetic acid and the 2-methylthio-5,6,8,9-tetrahydrothiopyrano[4,3-d]-1,2,4-triazolo[1,5-a]pyrimidine-5(10H)-one is precipitated again.

Thus 1.0 g of pure 2-methylthio-5,6,8,9-tetrahydrothiopyrano[4,3-d]-1,2,4-triazolo[1,5-a]pyrimidine-5(10H)-one is obtained with a melting point of 295°–297° C.

EXAMPLE 31

2-Dimethylamino-5,7,8,9-tetrahydrothiopyrano[3,2-d]-1,2,4-triazolo[1,5-a]pyrimidine-5(10H)-one The process of Example 19 is followed except that the reaction is carried out in 20 ml of butanol instead of the dimethylformamide/acetic acid mixture and the reaction mixture is boiled for 5 hours.

Yield: 7.4 g (58.9%).

Melting point: higher than 350° C. (after recrystallization from dimethylformamide).

EXAMPLE 32

2-Dimethylamino-5,7,8,9-tetrahydrothiopyrano[3,2-d]-1,2,4-triazolo[1,5-a]pyrimidine-5(10H)-one The process according to Example 19 is followed except that the reaction is carried out in the mixture of 10 ml of butanol and 5 ml of glacial acetic acid, instead of the mixture of dimethylformamide/acetic acid, and the mixture is boiled for 2 hours.

Yield: 8.5 g (67.6%).

M.p.: higher than 350° C. (after recrystallization from dimethylformamide).

EXAMPLE 33

2-Dimethylamino-5,7,8,9-tetrahydrothiopyrano[3,2-d]-1,2,4-triazolo[1,5-a]pyrimidine-5(10H)-one The process of Example 19 is followed except that the reaction is carried out in 20 ml of chlorobenzene instead of the mixture of dimethylformamide/acetic acid, and the mixture is boiled for 4 hours.

Yield: 7.1 g (55.7%).

M.p.: higher than 350° C. (after recrystallization from dimethylformamide).

EXAMPLE 34

2-Dimethylamino-5,7,8,9-tetrahydrothiopyrano[3,2-d]-1,2,4-triazolo[1,5-a]pyrimidine-5(10H)-one A mixture of 6.35 g (0.05 mole) of powdered 5-amino-3-dimethylamino-1H-1,2,4-triazole and 15 g (0.08 mole) of ethyl 3-oxo-3,4,5,6-tetrahydro-2H-thiopyrane-2-carboxylate is melted at 130° C. for 30 minutes. The melt is left to cool to about 80° C., then dissolved in 40 ml of hot 10% sodium hydroxide solution, the solution is clarified with charcoal, filtered off and left to crystallize. The precipitated crystals are filtered off, dissolved in 120 ml of distilled water, then the solution is acidified with acetic acid. The precipitated crystals are filtered off, thoroughly rinsed with water and dried.

Thus 7.6 g (60.5%) of pure product are obtained with a melting point higher than 350° C.

We claim:

1. Triazolo-pyrimidine derivatives of formulae Ia and Ib,

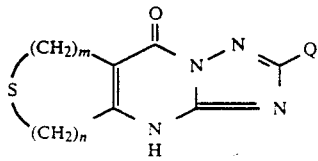

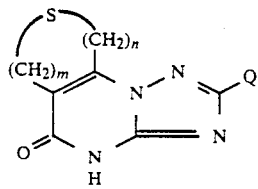

wherein

Q represents hydrogen, a 5- or 6-membered heterocyclic group comprising one or two nitrogen and/or oxygen atoms as the heteroatoms and optionally substituted by a $C_1$-$C_4$-alkyl group or a group of formula —$SR^1$ wherein $R^1$ is alkyl or aralkyl, or a group of formula —$NR^2R^3$ wherein $R^2$ and $R^3$ are independently hydrogen, alkyl, alkenyl, cycloalkyl, aralkyl, aryl, or a 5- or 6 membered heterocyclic group comprising one or two nitrogen and/or oxygen atoms as as heteroatoms and optionally substituted by halogen or $C_1$-$C_4$ alkyl groups m and n are independently 0, 1, 2, 3 or 4, with the proviso that if m stands for 0, then n is different from 0, and if both n and m are 1 or m stands for 0 and n is 2, then Q is not a methylthio or morpholino group, their mixtures or pharmaceutically acceptable salts.

2. Compounds of formulae Ia or Ib as claimed in claim 1, wherein Q represents —$NR^2R^3$, wherein $R^2$ and $R^3$ independently stand for alkyl having 1 to 6 carbon atoms optionally substituted by phenyl, alkenyl having 2 to 4 carbon atoms or cycloalkyl having 3 to 6 carbon atoms, phenylalkyl having 1 to 4 carbon atoms in the alkyl moiety.

3. Compound of formula Ia or Ib, wherein Q represents piperidino, morpholino or piperazino optionally substituted by alkyl having 1 to 4 carbon atoms.

4. Compounds of formula Ia or Ib as claimed in claim 1, wherein Q represents —$SR^1$, wherein $R^1$ stands for alkyl having 1 to 4 carbon atoms.

5. Pharmaceutically acceptable alkaline metal salts of compounds of formula Ia or Ib as claimed in claim 1.

6. Acid-addition salts of compounds of formula Ia or Ib as claimed in claim 5.

7. A pharmaceutical composition which comprises an analgesic or anti-depressant effective amount of from 1 to 10,000 mg of one or more compounds of formula Ia or Ib, wherein Q, n and m are the same as defined in claim 1, their mixture or pharmaceutically acceptable salts as active ingredient.

* * * * *